United States Patent [19]

Chen

[11] 4,221,717
[45] Sep. 9, 1980

[54] TOTAL SYNTHESIS OF THE UTERO-EVACUANT SUBSTANCE D,L-ZOAPATANOL

[75] Inventor: Robert H. K. Chen, Belle Mead, N.J.

[73] Assignee: Ortho Pharmaceutical Corporation, Raritan, N.J.

[21] Appl. No.: 23,492

[22] Filed: Mar. 23, 1979

Related U.S. Application Data

[62] Division of Ser. No. 920,433, Jun. 29, 1978.

[51] Int. Cl.$^2$ ............................................. C07D 313/04
[52] U.S. Cl. .................................. 260/333; 260/340.7; 260/340.9 R; 260/345.9 R; 260/348.48; 260/348.57; 424/278
[58] Field of Search ......................................... 260/333

[56] References Cited

U.S. PATENT DOCUMENTS

| 4,086,358 | 4/1978 | Wachter et al. | 260/333 |
| 4,102,895 | 7/1978 | Kanojia et al. | 260/333 |

Primary Examiner—Henry R. Jiles
Assistant Examiner—Jane T. Fan
Attorney, Agent, or Firm—Benjamin F. Lambert

[57] ABSTRACT

A method of synthesizing 2S*, 3R*-6E-(2-hydroxyethylidene)-2-methyl-2-(4,8-dimethyl-5-oxo-7-nonenyl)-oxepan-3-ol, one of the active ingredients in the zoapatle plant, is described. The active ingredients in the plant are useful as utero-evacuant agents.

6 Claims, No Drawings

TOTAL SYNTHESIS OF THE UTERO-EVACUANT SUBSTANCE D,L-ZOAPATANOL

This is a division, of application Ser. No. 920,433, filed June 29, 1978.

The zoapatle plant is a bush about 2 meters high that grows wild in Mexico. Botanically it is known as *Montanoa tomentosa* according to Cervantes, Fam. Compositae, Tribe Heliantheae; another variety of the species is *Montanoa floribunda*. The plant is described in great detail in *Las Plantas Medicinales de Mexico*, Third Edition, Ediciones Botas (1944).

The zoapatle plant has been used for centuries in the form of a "tea" or other crude aqueous preparations primarily as a labor inducer or menses inducer for humans. Its use as a utero-evacuant agent has been documented in the literature.

In U.S. Pat. No. 4,086,358, a method is described for the isolation of the active ingredients in the zoapatle plant. One of the active ingredients is 2S, 3R-6E-(2-hydroxyethylidene)-2-methyl-2-(4,8-dimethyl-5-oxo-7-nonenyl)-oxepan-3-ol. This compound, referred to as zoapatanol, has the following structural formula:

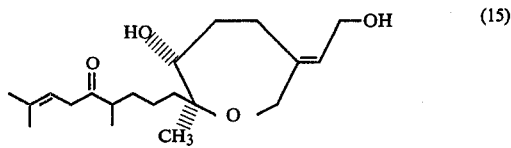

The present invention relates to a method for the total synthesis of 2S*,3R*-6E-(2-hydroxyethylidene)-2-methyl-2-(4,8-dimethyl-5-oxo-7-nonenyl)-oxepan-3-ol. Many of the intermediates employed in the synthesis of zoapatanol are novel compounds and are included as part of the invention.

[*The asterisk indicates the racemic nature of the compound and refers to the relative configuration of the chiral centers.]

The synthesis is comprised of several steps which are summarized in the following schematic diagram:

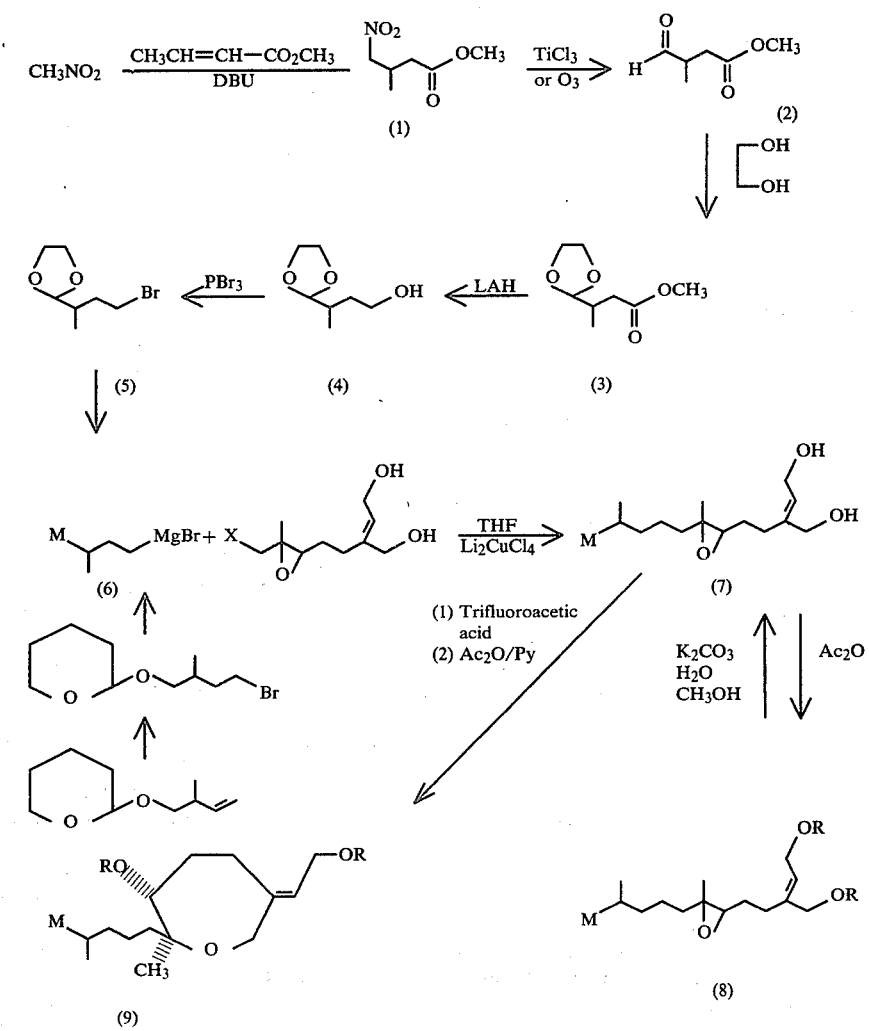

-continued

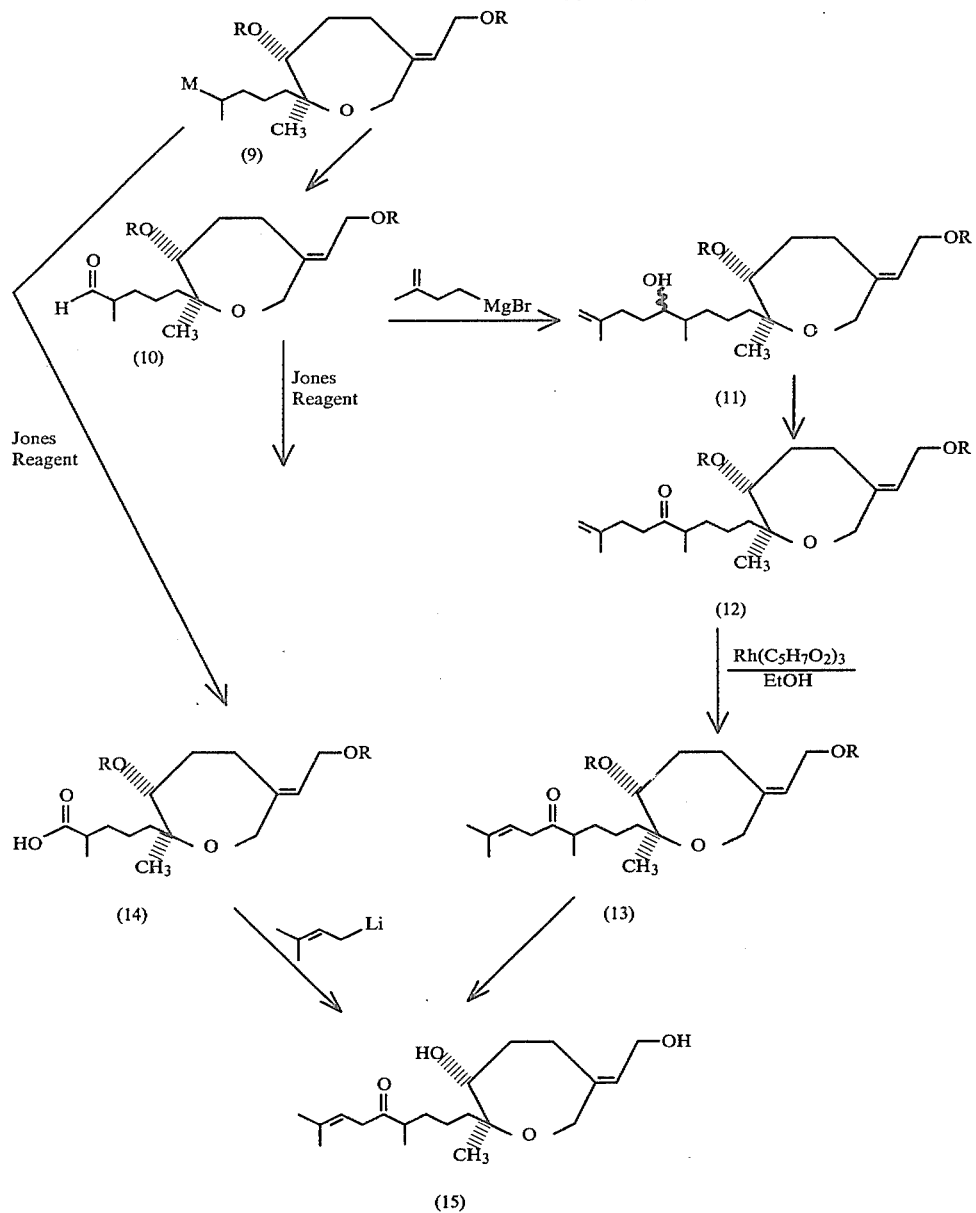

wherein DBU is 1,5-diazabicyclo[5,4,0]undec-5-ene, M is selected from the group consisting of ethylenedioxymethyl, 4-methyl-1,3-ethylenedioxymethyl, 1,3-propylenedioxymethyl, and (tetrahydropyran-2-yloxy)methyl, X is selected from the group consisting of tosyl, mesyl, brosyl, bromo, chloro and iodo, and R is an acyl group having 2–5 carbon atoms.

As can be seen from the diagram the first step in the synthesis involves the preparation of the nitro ester derivative (1). This compound is prepared by reacting nitromethane with methyl crotonate in the presence of a base such as, for example, 1,5-diazabicyclo [5,4,0]undec-5-ene, sodium methoxide and potassium t-butoxide. It is preferred to use an excess of methyl crotonate in the reaction and the reaction is preferably carried out in an organic solvent. Suitable solvents which can be employed include methanol, ethanol, t-butanol and the like. The reaction may be carried out at room temperature or at elevated temperatures such as, for example, the reflux temperature of the solvent. The nitro ester derivative (1) is isolated by techniques known to those skilled in the art. One method, for example, involves the removal of the base by washing the reaction mixture with a dilute aqueous acid followed by purification of the crude product by column chromatography over an adsorbent material such as silica gel, alumina or florisil. Purification can also be achieved by distillation.

The nitro ester derivative (1) is then converted to the ester (2) by treatment with titanous chloride in the presence of a base. Suitable bases which can be employed include sodium methoxide, sodium ethoxide and potassium t-butoxide, for example. It is preferred to use one equivalent of the base. The reaction is preferably carried out in an inert atmosphere such as nitrogen or argon at a temperature between 0° and 30° C. Solvent systems which can be employed for the reaction include aqueous alcoholic solutions such as, for example, methanol-water, ethanol-water and isopropanol-water. Alternatively, the ester (2) can be prepared by reacting the nitro ester derivative (1) with ozone in the presence of a base such as sodium methoxide, sodium ethoxide or potassium t-butoxide. The oxidation with ozone is carried out preferably at a temperature between −78° and −50° C. Solvents such as methanol and ethanol may be employed. It is preferred to employ one equivalent of the base in the oxidation step.

The acetal ester (3) is prepared by reacting the ester (2) prepared above with ethylene glycol. Other diols which can be employed include 1,2-propanediol and 1,3-propanediol. The reaction is preferably carried out with an excess of the diol in an inert atmosphere such as nitrogen or argon in the presence of a catalytic amount of an acid such as p-toluenesulfonic acid monohydrate, concentrated sulfuric acid and concentrated hydrochloric acid. Solvents such as benzene and toluene may be employed, and it is preferred to carry out the reaction at the reflux temperature of the solvent.

The acetal ester is reduced to the alcohol (4) by treatment with a reducing agent such as, for example, lithium aluminum hydride. It is preferred to use a slight excess of the reducing agent in this step. The reduction is generally carried out in an organic solvent such as ether or tetrahydrofuran at a temperature between about 0° and 30° C. The alcohol (4) is isolated from the reaction mixture by methods known to those skilled in the art. Generally, the reaction mixture is quenched with dilute aqueous base such as a 5% aqueous solution of sodium bicarbonate, potassium hydroxide, potassium carbonate, sodium hydroxide or sodium carbonate and the like. The product can be purified by column chromatography on an adsorbent material such as silica gel or florisil.

The alcohol (4) is converted to the corresponding bromide derivative (5) by reaction with a brominating agent in the presence of an organic base such as pyridine or triethylamine, for example. Suitable brominating agents which can be employed include phosphorous tribromide, carbon tetrabromide-triphenyl phosphine, carbon tetrabromide-tri-n-butyl phosphine and triphenyl phosphine-bromine. An excess of the brominating agent is generally employed and the reaction is preferably carried out at a temperature between 0° and 30° C. Solvents which may be employed in the bromination reaction include hexane, benzene, ether, methylene chloride, chloroform and the like. The brominated compound can be isolated from the reaction mixture by techniques known to those skilled in the art. The organic base, for example, can be removed by washing the reaction mixture with a dilute aqueous acid such as 10% hydrochloric acid or dilute sulfuric acid, or an aqueous saturated solution of a copper salt such as copper sulfate. The bromide derivative (5) can be purified by known techniques including column chromatography over a suitable adsorbent such as silica gel, alumina and florisil, or by distillation. In those cases where M is (tetrahydropyran-2-yloxy)methyl the Grignard reagent (6) is prepared from 1-bromo-3-methyl-4-(tetrahydropyran-2-yloxy)-butane. The bromo butane derivative is prepared by reacting 3-methyl-4-(tetrahydropyran-2-yloxy)-1-butene first with diborane followed by reaction with bromine in the presence of a base such as sodium methoxide or sodium ethoxide. The reaction is carried out at a temperature between 0° C. and room temperature in a suitable solvent such as ether or tetrahydrofuran.

The Grignard reagent (6) is prepared from the bromide derivative (5) by reaction with magnesium according to standard techniques for preparing such reagents. Solvents which can be employed for the reaction include ether and tetrahydrofuran. The Grignard reagent is generally not isolated but is used as such in the next step in the synthesis.

The coupled product (7) is prepared by treating the Grignard reagent (6) with a substituted 7-methyl-3-hydroxymethyl-6,7-oxido-(E)-2-octen-1-ol compound in the presence of a catalytic amount of a copper salt such as cuprous iodide, cuprous bromide, or lithium copper chloride. The reaction is preferably carried out at a temperature between about −20° and 0° C. Solvents which may be employed for the coupling reaction include ether and tetrahydrofuran, for example. The coupled product (7) can be used directly in the cyclization step or it can be purified first by converting it to the diacyl derivative (8) by reaction with a suitable acylating agent such as acetic anhydride in the presence of a base such as pyridine.

The oxepane derivative (9) is prepared from the coupled product (7) by reaction with a Lewis acid such as boron trifluoride etherate, for example, or a protic acid such as trifluoroacetic acid followed by acylation of the hydroxyl groups. The cyclization reaction is carried out at a temperature between 0° and 30° C. in an organic solvent such as benzene, chloroform, methylene chloride and the like. It is preferred to use a catalytic amount of the acid. The reaction mixture is then converted to the diacyl derivative (9) by reaction with an acylating agent. Suitable acylating agents include acyl halides having 2–5 carbon atoms in the acyl group and acid anhydrides having 2–5 carbon atoms in the alkyl group. The acylation step is carried out by general techniques known to those skilled in the art.

The oxepane derivative (9) is hydrolyzed to the aldehyde derivative (10) by treatment with a suitable protic acid such as, for example, dilute sulfuric acid, p-toluenesulfonic acid monohydrate and glacial acetic acid. The hydrolysis reaction may be carried out at room temperature or at elevated temperature, preferably at the reflux temperature of the solvent employed. It is preferred to carry out the reaction in an inert atmosphere such as nitrogen or argon. Solvent systems which may be employed for the hydrolysis step include acetone-water, tetrahydrofuran-water and 1,4-dioxane-water. The aldehyde can be further purified by column chromatography on an adsorbent material such as silica gel, alumina or florisil. In the case where M is (tetrahydropyran-2-yloxy)methyl the aldehyde (10) is obtained by hydrolyzing the cyclized product (9) in the presence of an acid such as acetic acid in a suitable solvent such as tetrahydrofuran. The hydrolysis is preferably carried out at a temperature between room temperature and 60° C. in an inert atmosphere such as nitrogen or argon. The alcohol formed on hydrolysis is then converted to the aldehyde (10) by oxidation with an oxidizing agent such as chromium trioxide-pyridine. The oxidation is carried out at a temperature between −10° and 25° C. in an organic solvent such as methylene chloride, chloroform and the like.

The aldehyde (10) is converted to the alcohol (11) by reaction with 3-methyl-3-butenyl magnesium bromide. The reaction is preferably carried out with an equivalent amount of the Grignard reagent under an inert atmosphere such as nitrogen or argon at a temperature between −78° and −20° C. The addition reaction can be carried out in an organic solvent such as, for example, ether or tetrahydrofuran. The addition product (11) can be isolated from the reaction mixture by first treating the reaction mixture with a dilute aqueous acid solution such as saturated ammonium chloride solution or 5% hydrochloric acid solution followed by extraction with an organic solvent. The crude alcohol (11) can be purified by chromatography on a suitable adsorbent material such as silica gel, alumina or florisil. Other techniques generally known to those skilled in the art may be employed to isolate and purify the alcohol.

The alcohol (11) is then oxidized to the keto derivative (12) by reaction with a suitable oxidizing agent. Oxidizing agents which can be employed include chromium trioxide-sulfuric acid (Jones Reagent) and chromium trioxide-pyridine. The oxidation reaction is preferably carried out at between $-10°$ and $25°$ C. in an organic solvent such as, for example, 2-butanone, acetone, methylene chloride and chloroform. The particular solvent employed will depend upon the oxidizing agent employed. The crude keto derivative (12) can be further purified by column chromatography on silica gel.

The keto derivative (12) can be isomerized to a diacyl derivative of zoapatanol (13) by reaction with a transition metal complex such as rhodium (III) 2,4-pentandionate. The isomerization is preferably carried out in an alcoholic solvent such as ethanol or isopropanol. The diacyl derivative is converted to zoapatanol (15) by hydrolysis according to conventional hydrolysis techniques.

The aldehyde (10) may be converted to the acid derivative (14) by reaction with a suitable oxidizing agent such as, for example, chromium trioxide-sulfuric acid (Jones Reagent). The reaction can be carried out at room temperature in an organic solvent such as, for example, acetone or 2-butanone. Alternatively, the oxepane derivative (9) can be converted directly to the acid derivative (14) by reaction with chromium trioxidesulfuric acid (Jones Reagent). The crude acid (14) is then converted to racemic zoapatanol (15) by reaction with 3-methyl-2-butenyl lithium. It is preferred to use an excess of the lithium compound. The addition may be carried out in an organic solvent such as ether, tetrahydrofuran or an ether-tetrahydrofuran mixture. The crude product (15) can be purified by column chromatography on an adsorbent material such as silica gel, alumina or florisil.

The substituted 7-methyl-3-hydroxymethyl-6,7-oxido-(E)-2-octen-1-ol compounds which are used to prepare the coupled product (7) are prepared from 8-hydroxy-7-methyl-3-methylene-1,6(E)-octadiene.
The octadiene compound is synthesized from myrcene according to the method of Büchi et al. [G. Büchi and H. Wüest, Helv. Chim. Acta, 50, 2440 (1967)]. The octadiene compound is first converted to the hydroxy epoxide by treatment with with a peracid, such as peracetic acid or m-chloroperbenzoic acid. The reaction is carried out at a temperature between $-20°$ and $30°$ C. in a suitable solvent such as methylene chloride or chloroform. The crude product is purified by chromatography or distillation. The epoxide is then converted to the bis acyl derivative by treatment with an equivalent amount of a halogen, such as bromine, followed by an excess of an acetate salt such as potassium acetate. The bromination is carried out in an organic solvent such as methylene chloride, chloroform or carbon tetrachloride. The substitution of bromide with acetate is carried out in a mixture of water and an organic solvent such as carbon tetrachloride preferably in the presence of a phase transfer agent such as benzyltriethyl ammonium chloride and adogen 464. The major product of the reaction is the compound having the E configuration, however, about 20% of the compound having the Z configuration is also formed. The product is purified by chromatography and treatment of the acetate with a slight excess of p-toluenesulfonyl chloride in the presence of a base such as pyridine or triethylamine gives the tosylate derivative. The reaction is preferably carried out at a temperature between $0°$ and $60°$ C. in an inert atmosphere. Solvents such as ether or tetrahydrofuran may be employed. Hydrolysis of the tosylate derivative with a base such as sodium bicarbonate, potassium carbonate, sodium hydroxide or tetra-n-butyl ammonium hydroxide gives the tosylate derivative of 7-methyl-3-hydroxymethyl-6,7-oxido-(E)-2-octen-1-ol. The hydrolysis is carried out at room temperature or at elevated temperatures, preferably, the reflux temperature of the solvent. Solvent systems such as methanol-water, ethanol-water, benzene-water or tetrahydrofuran-water may be employed. The bromo substituted compound is prepared in the same manner by reacting 1-acetoxy-8-hydroxy-7-methyl-3-acetoxymethyl-6,7-oxido-(E)-2-octene with a brominating agent such as phosphorous tribromide using a base such as pyridine as the catalyst. Solvents such as ether or tetrahydrofuran can be employed in the bromination reaction. Hydrolysis of the ester in the presence of a base such as sodium hydroxide, for example, yields the free alcohol. During the workup of the reaction mixture, the compound having the Z configuration forms a complex with magnesium sulfate which results in a product having only the E configuration. Those compounds wherein X is mesyl and brosyl are prepared in the same manner in which the tosylate is prepared but substituting mesyl chloride and p-bromosulfonyl chloride for p-toluenesulfonyl chloride.

The material obtained by the above synthesis compares favorably with the natural product obtained and characterized in U.S. Pat. No. 4,086,358.

The following examples describe the invention in greater detail and are intended to be a way of illustrating and not limiting the invention.

EXAMPLE 1

Methyl 3-methyl-4-nitrobutanoate 1,5-Diazabicyclo[5,4,0]-undec-5-ene (6 ml) is added to a solution of nitromethane (91.5 g) in methanol (500 ml). The resulting mixture is heated to 60° C. and methyl crotonate (100 g, 1m) is added under nitrogen. The mixture is then stirred for 6 days at 60° after which it is cooled to room temperature and most of the methanol is removed in vacuo. The residue is treated with ether (500 ml) and washed with 2 N hydrochloric acid (250 ml) and water (250 ml). The organic layer is dried (Na$_2$SO$_4$) and evaporated in vacuo to give crude product. The crude product is purified by column chromatography on silica gel (500 g, ethyl acetate/hexane 2:98) to give methyl 3-methyl-4-nitrobutanoate (106.6 g, 66%).

ir (neat) 1735 and 1550 cm$^{-1}$; nmr (CDCl$_3$)δ: 0.95 (d, J=6 Hz, 3H,

3.68 (s, 3H, -CO₂CH₃), 4.42 (pair of doublets, J=6 Hz each, 2H,

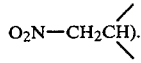

EXAMPLE 2

Methyl 3-methyl-4-oxo-butanoate (a) A solution of methyl 3-methyl-4-nitrobutanoate (24.55 g) in methanol (10 ml) is added dropwise to a solution of sodium methoxide (6.37 g) in methanol (250 ml) at room temperature under nitrogen. The resulting mixture is stirred for one hour, added to a mixture of 20% titanous chloride (170 ml), and pH 7 buffer (potassium phosphate monobasic-sodium hydroxide buffer) solution (340 ml) and stirred for 30 minutes. The mixture is then treated with ether (1 l). The organic phase is separated, dried (Na₂SO₄) and evaporated in vacuo to give the crude product. The crude material is purified by column chromatography on silica gel (300 g, 2% ethyl acetate in hexane, to give methyl 3-methyl-4-oxo butanoate as a colorless liquid. This material is used directly in the next step.

(b) A solution of methyl 3-methyl-4-nitrobutanoate (96 g, 0.596 m) in methanol (30 ml) is added dropwise to a solution of sodium methoxide (34.5 g, 0.638 m) in methanol (1 l) at room temperature under nitrogen. The resulting mixture is stirred for 1 hr., cooled to −78° C. and treated with one equivalent of ozone. The reaction mixture is then allowed to warm to room temperature and most of the solvent is removed in vacuo. The residue is filtered and the filtrate is treated with ether (500 ml). The organic phase is washed with water (3×200 ml), dried (Na₂SO₄) and the solvent is removed in vacuo to give the crude product, methyl 3-methyl-4-oxo-butanoate (86.3 g). This material is used directly in the next step.

EXAMPLE 3

Methyl 4,4-ethylenedioxy-3-methyl-butanoate

A mixture of methyl 3-methyl-4-oxo-butanoate (86.3 g), ethylene glycol (61.75 1 g, 0.996 m), p-toluenesulfonic acid (1 g) and benzene (700 ml) is refluxed under nitrogen for 16 hr. The resulting mixture is allowed to cool to room temperature and treated with ether (300 ml). The organic phase is washed with 5% sodium bicarbonate solution (100 ml), dried (Na₂SO₄) and evaporated in vacuo to give methyl 4,4-ethylenedioxy-3-methylbutanoate as a crude product (63.2 g). This material is used directly in the next step.

EXAMPLE 4

4,4-Ethylenedioxy-3-methyl-1-butanol

A solution of methyl 4,4-ethylenedioxy-3-methyl-butanoate (63.2 g) in ether (200 ml) is added dropwise to a mixture of lithium aluminum hydride (13.8 g, 0.363 m) in ether (500 ml) at 0° C. under nitrogen. The resulting mixture is stirred for 2 hr., treated with 5% sodium bicarbonate solution (100 ml), allowed to warm to room temperature and filtered. The filtrate is dried (Na₂SO₄) and the solvent is evaporated in vacuo to give the crude product (26 g). This material is further purified by column chromatography on silica gel (300 g, 20% ethyl acetate in hexane) to give 4,4-ethylenedioxy-3-methyl-1-butanol as a colorless liquid (14.9 g).

ir (neat) 3440 cm⁻¹, nmr (CDCl₃)δ: 0.97 (d, J=7 Hz, 3H, -CHC$\underline{H}$₃), 3.53–3.88 (m, 6H,

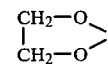

and -C$\underline{H}$₂OH), 4.65 (d, J=4 Hz, 1H,

EXAMPLE 5

1-Bromo-4,4-ethylenedioxy-3-methyl-butane

A solution of 4,4-ethylenedioxy-3-methyl-1-butanol (30 g, 0.205 m) in triethylamine (75 ml) is added dropwise to a mixture of phosphorous tribromide (63.36 g, 0.228 m) and petroleum ether (100 ml) at room temperature. After the addition is complete, the resulting mixture is heated at 60° C. for 3 hrs., cooled to 0° C. and treated with ether (300 ml). The ether mixture is then poured into cold 5% sodium bicarbonate solution (100 ml). The organic phase is separated, dried (Na₂SO₄) and evaporated to give a pale yellow liquid (31 g). The crude product is further purified by column chromatography on silica gel (100 g, 10% ether in petroleum ether) to give 1-bromo-4,4-ethylenedioxy-3-methyl-butane as a colorless liquid (9.9 g, 23%).

nmr (CDCL₃)δ: 0.97 (d, J=7 Hz, 3H,

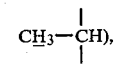

3.50 (bt, J=6 Hz, 2H, -CH₂-C$\underline{H}$₂Br), 3.85 (b, 4H, -OC$\underline{H}$₂C$\underline{H}$₂-O-), 4.64 (d, J=4 Hz, 1H,

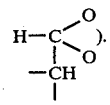

EXAMPLE 6

8-hydroxy-7-methyl-3-methylene-6,7-oxido-1-octene

A solution of sodium acetate (25 g, 0.03 m) in 40% peracetic acid (85 ml) is added to a mixture of 8-hydroxy-7-methyl-3-methylene-1,6(E)-octadiene (50.0 g, 0.33 m), sodium carbonate (42.4 g, 0.40 m) and methylene chloride (500 ml) at 0°. The resulting mixture is allowed to come to room temperature, stirred for an additional hour and then filtered, diluted with methylene chloride (1 l) and washed with 5% sodium bicarbonate soluton (2 l). The organic layer is dried (Na₂SO₄), and evaporated in vacuo to give 8-hydroxy-7- methyl-3-methylene-6,7-oxido-1-octene as a crude product (49.5 g).

The crude product is purified by column chromatography on silica gel (600 g; ethyl acetate/hexane 1:9) to give 8-hydroxy-7-methyl-3-methylene-6,7-oxido-1-octene (23.2 g, 42%).

ir (neat): 3448, 1592, cm$^{-1}$; nmr (CDCl$_3$)δ: 1.25 (s, 3H,

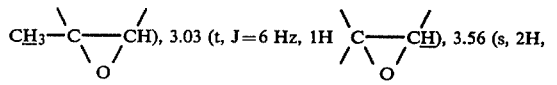
C$\underline{H}_3$—C——CH), 3.03 (t, J=6 Hz, 1H, C——C$\underline{H}$), 3.56 (s, 2H,

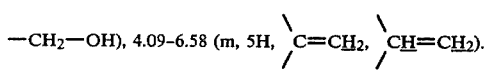
—CH$_2$—OH), 4.09–6.58 (m, 5H, C=C$\underline{H}_2$, C$\underline{H}$=C$\underline{H}_2$).

EXAMPLE 7

1-Acetoxy-8-hydroxy-7-methyl-3-acetoxymethyl-6,7-oxido-(E)-2-octene

Bromine (56.8 g, 0.355 m) is added to a solution of 8-hydroxy-7-methyl-3-methylene-6,7-oxido-1-octene (59.7 g, 0.355 m) in methylene chloride (1 l) under nitrogen at 0° C. and the resulting mixture is then allowed to warm to room temperature. The mixture is washed with water (500 ml), the organic layer is dried (Na$_2$SO$_4$) and the solvent removed to give the crude dibromide (117.0 g).

A portion of the crude dibromide (57.2 g) in carbon tetrachloride (50 ml) is added to a solution of potassium acetate (59.8 g, 0.61 m) and adogen 464 (15.0 g) in water at 60° C. The resulting mixture is stirred overnight, and then cooled to room temperature, diluted with ether (1 l) and washed with water (500 ml). The organic layer is dried (Na$_2$SO$_4$) and evaporated in vacuo to give the crude diacetate (64.0 g). The crude product is further purified by column chromatography on silica gel (2 kg, ethyl acetate/hexane 4:6) to give 1-acetoxy-8-hydroxy-7-methyl-3-acetoxymethyl-6,7-oxido-(E)-2-octene (9.5 g; 18%).

ir (neat) 3484, 1730 cm$^{-1}$; nmr (CDCl$_3$)δ: 1.28 (s, 3H,

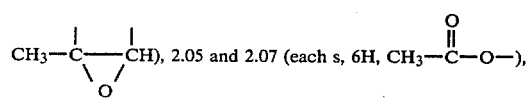
CH$_3$—C——CH), 2.05 and 2.07 (each s, 6H, CH$_3$—C—O—),

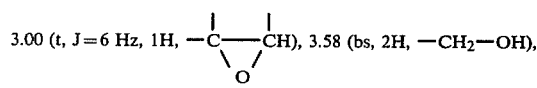
3.00 (t, J=6 Hz, 1H, —C——CH), 3.58 (bs, 2H, —CH$_2$—OH),

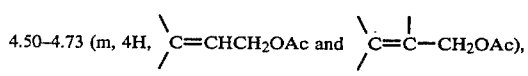
4.50–4.73 (m, 4H, C=CHCH$_2$OAc and C=C—CH$_2$OAc),

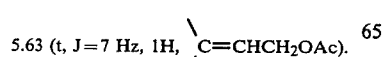
5.63 (t, J=7 Hz, 1H, C=CHCH$_2$OAc).

EXAMPLE 8

1-Acetoxy-7-methyl-3-acetoxymethyl-6,7-oxido-8-tosyloxy-(E)-2-octene

Triethylamine (10 ml) and tosyl chloride (13.78 g, 0.072 m) are added to a solution of 1-acetoxy-8-hydroxy-7-methyl-3-acetoxymethyl-6,7-oxido-(E)-2-octene (10.34 g, 0.036 m) in dry tetrahydrofuran (300 ml). The resulting mixture is stirred at room temperature under nitrogen for 6 days and then diluted with ether (800 ml) and washed with 5% sodium bicarbonate solution (800 ml) and water (800 ml). The organic layer is dried (Na$_2$SO$_4$) and evaporated in vacuo to give the crude product (18.3 g). This material is purified by column chromatography on silica gel (600 g; ethyl acetate/hexane; 40:60) to give 1-acetoxy-7-methyl-3-acetoxymethyl-6,7-oxido-8-tosyloxy-(E)-2-octene (10.12 g, 64%).

ir (neat) 1730, 1595 cm$^{-1}$; nmr (CDCl$_3$)δ: 1.28 (s, 3H,

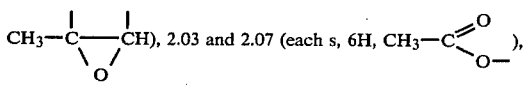
CH$_3$—C——CH), 2.03 and 2.07 (each s, 6H, CH$_3$—C$\overset{O}{\underset{O-}{}}$ ),

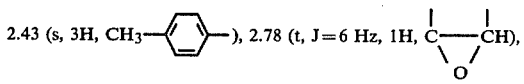
2.43 (s, 3H, CH$_3$—⟨⟩—), 2.78 (t, J=6 Hz, 1H, C——CH),

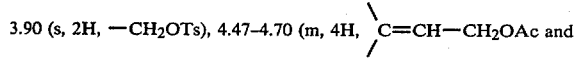
3.90 (s, 2H, —CH$_2$OTs), 4.47–4.70 (m, 4H, C=CH—CH$_2$OAc and

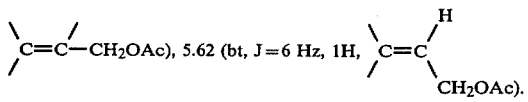
C=C—CH$_2$OAc), 5.62 (bt, J=6 Hz, 1H, C=C$\overset{H}{\underset{CH_2OAc}{}}$).

EXAMPLE 9

7-Methyl-3-hydroxymethyl-6,7-oxido-8-tosyloxy-(E)-2-octen-1-ol

A mixture of 1-acetoxy-7-methyl-3-acetoxymethyl-6,7-oxido-8-tosyloxy-(E)-2-octene (4.0 g, 9.1 mmole), methanol (150 ml), water (5 ml) and saturated potassium carbonate solution (5 ml) is stirred at room temperature for 2 hr. Most of the methanol is then removed in vacuo and the resulting mixture is extracted with ethyl acetate (3×20 ml). The combined organic layer is dried (MgSO$_4$) and evaporated in vacuo to give an oil (3.4 g). The oil is further purified by column chromatography on silica gel (20 g, isopropanol/chloroform 2:98) to give 7-methyl-3-hydroxymethyl-6,7-oxido-8-tosyloxy-(E)-2-octen-1-ol as a colorless oil (2.24 g, 69%).

ir (neat) 3424, 1597 cm$^{-1}$; nmr (CDCl$_3$)δ: 1.28 (s, 3H,

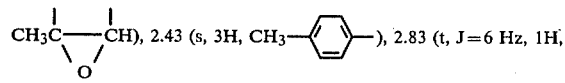
CH$_3$C——CH), 2.43 (s, 3H, CH$_3$—⟨⟩—), 2.83 (t, J=6 Hz, 1H,

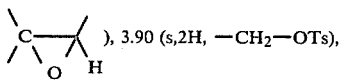
), 3.90 (s, 2H, —CH$_2$—OTs),

-continued 5.70 (bt, J=6 Hz, 1H, 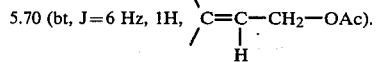

EXAMPLE 10

1-Acetoxy-3-acetoxymethyl-7,11-dimethyl-12,12-ethylenedioxy-6,7-oxido-(E)-2-dodecene A solution of 1-bromo-4,4-ethylenedioxy-3-methylbutane (10 g, 47.3 mmole) in tetrahydrofuran (95 ml) is added to a suspension of magnesium turnings (2.2 g, 91 mmole) in tetrahydrofuran (5 ml) at room temperature under nitrogen over a period of four hours. An excess of the Grignard reagent is then added to a solution of 7-methyl-3-hydroxymethyl-6,7-oxido-8-tosyloxy-(E)-2-octen-1ol (800 mg) in tetrahydrofuran at 0°, followed by Li$_2$CuCl$_4$ (0.1 mmole) and stirred for 1.5 hours at 0°. The mixture is allowed to warm to room temperature and then treated with ice water (125 ml) and ethyl acetate (400 ml). The organic phase is separated, dried (Na$_2$SO$_4$) and evaporated in vacuo to give the crude product, 7,11-dimethyl-12,12-ethylenedioxy-3-hydroxymethyl-6,7-oxido-(E)-2-dodecen-1-ol. The product is treated with acetic anhydride (10 ml) and pyridine (2 ml) and stirred for 16 hr. at room temperature. The resulting mixture is treated with ether (100 ml) and then washed with saturated cupric sulfate solution (100 ml) and 5% sodium bicarbonate solution (100 ml). The organic phase is dried (Na$_2$SO$_4$) and evaporated in vacuo to give an oil. This material is further purified by column chromatography on silica gel (7 g, 7% ethyl acetate in hexane) to give 1-acetoxy-3-acetoxymethyl-7,11-dimethyl-12,12-ethylenedioxy-6,7-oxido-(E)-2-dodecene as a colorless oil (350 mg, 25%):

ir (neat), 1735 cm$^{-1}$; nmr (CDCl$_3$)δ: 0.98 (d, J=7 Hz, 3H,

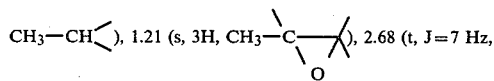

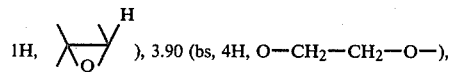

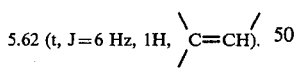

EXAMPLE 11

2S*, 3R*-3-Acetoxy-6E-(2-acetoxyethylidene)-2-methyl-2-(5,5-ethylenedioxy-4-methylpentyl)-oxepane A mixture of 1-acetoxy-3-acetoxymethyl-7,11-dimethyl-12,12-ethylenedioxy-6,7-oxido-(E)-2-dodecene (10 mg.), methanol (5 ml), saturated potassium carbonate solution (1 ml) and water (1 ml), is stirred at room temperature for 3 hr. The mixture is then treated with ethyl acetate (15 ml) and water (15 ml), the organic phase is dried (Na$_2$SO$_4$) and the solvent removed in vacuo to give a colorless oil. The oil is dissolved in methylene chloride (5 ml) and treated with trifluoroacetic acid (5 drops) and stirred for 90 min. at room temperature. The resulting mixture is treated with pyridine (2 ml) and acetic anhydride (1 ml) and stirred for 16 hr. Most of the solvent is evaporated in vacuo and the residue (15 mg) is purified by column chromatography on silica gel (1 g, 20% ether in petroleum ether to give 2S*, 3R*-3-acetoxy-6E-(2-acetoxyethylidene)-2-methyl-2-(5,5-ethylenedioxy-4-methylpentyl)-oxepane as a colorless oil (50%).

ir (neat): 1735 cm$^{-1}$, nmr (CDCl$_3$)δ: 0.96 (d, J=7 Hz, 3H,

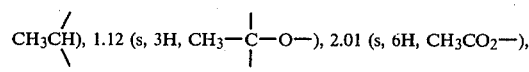

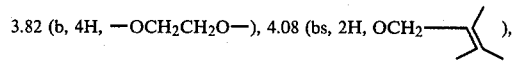

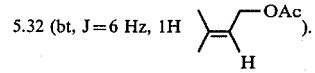

EXAMPLE 12

2S*, 3R*-3-Acetoxy-6E-(2-acetoxyethylidene)-2-methyl-2-(4-methyl-5-oxopentyl)-oxepane A mixture of 2S*, 3R*-3-acetoxy-6E-(2-acetoxyethylidene)-2-methyl-2-(5,5-ethylenedioxy-4-methylpentyl)-oxepane (230 mg, 0.578 mmole), acetic acid (3 ml), tetrahydrofuran (10 ml) and water (1.5 ml) is stirred at 60° under nitrogen for 5 hr. The resulting mixture is cooled to room temperature and treated with ether (50 ml). The organic phase is washed with 5% sodium bicarbonate solution (3×5 ml), water (50 ml), dried (Na$_2$SO$_4$) and evaporated to give a crude product (150 mg). The crude material is purified by column chromatography on silica gel (30 g, 30% ether in petroleum ether) to give 2S*, 3R*-3-acetoxy-6E-(2-acetoxyethylidene)-2-methyl-2-(4-methyl-5-oxopentyl)-oxepane as a colorless oil (120 mg).

ir (neat): 2660, 1740 (shoulder), 1735 cm$^{-1}$.

EXAMPLE 13

2S*, 3R*-3-Acetoxy-6E-(2-acetoxyethylidene)-2-methyl-2-(4,8-dimethyl-5-hydroxy-8-nonenyl)-oxepane One equivalent of 3-methyl-3-butenyl magnesium bromide in tetrahydrofuran is added dropwise to a solution of 2S*, 3R*-3-acetoxy-6E-(2-acetoxyethylidene)-2-methyl-2-(4-methyl-5-oxopentyl)-oxepane (20 mg., 0.056 mmole) in tetrahydrofuran (2 ml) at −78° under argon. The resulting mixture is stirred for 30 min., treated with methanol (1 ml) and then allowed to warm to room temperature, after which it is treated with ether (20 ml). The organic phase is washed with water (10 ml), dried (Na$_2$SO$_4$) and evaporated in vacuo to give a crude product. The crude material is purified by column chromatography on silica gel (10 g, 50% ether in petroleum ether) to give 2S*, 3R*-3-acetoxy-6E-(2-acetoxyethylidene)-2-methyl-2-(4,8-dimethyl-5-hydroxy-8-nonenyl)-oxepane as a colorless oil (15 mg, 62%).

ir (neat), (CDCL$_{1735, 1250, 1030, 890}$ cm$^{-1}$; nmr (CDCL$_3$)δ:

1.13 (s, 3H, CH₃—C—O), 1.72 (bs, 3H, 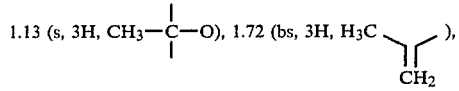), 2.02 (s, 6H, CH₃CO₂—), 4.08 (bs, 2H, 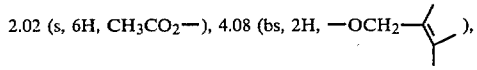), 5.32 (bt, J=6 Hz, 1H, 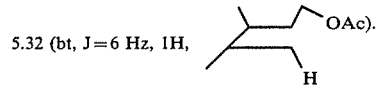).

EXAMPLE 14

2S*, 3R*-3-Acetoxy-6E-(2-acetoxyethylidene)-2-methyl-2-(4,8-dimethyl-5-oxo-8-nonenyl)-oxepane A slight excess of Jones reagent is added dropwise t a solution of 2S*, 3R*-3-acetoxy-6E-(2-acetoxyethylidene)-2-methyl-2-(4,8-dimethyl-5-hydroxy-8-nonenyl)-oxepane (15 mg, 0.035 mmole) in acetone (3 ml) at 0° under nitrogen. The mixture is stirred for 30 min., treated with 2-propanol (1 ml) and allowed to warm to room temperature. The resulting mixture is treated with potassium carbonate (30 mg) and filtered through a silica gel column (5 g). The column is washed with ether: petroleum ether (1:1, 50 ml) collecting one fraction. The solvent is removed in vacuo and the residue is purified by column chromatography on silica gel (15 g, 30% ether in petroluem ether) to give 2S*, 3R*-3-acetoxy-6-E-(2-acetoxyethylidene)-2-methyl-2-(4,8-dimethyl-5-oxo-8-nonenyl)-oxepane as a colorless oil (11 mg, 73%).

ir (neat), 1735, 1710 (shoulder), 1245, 890 cm⁻¹; nmr (CDCl₃)δ:

1.12 (s, 3H, CH₃—C—O), 1.76 (bs, 3H, 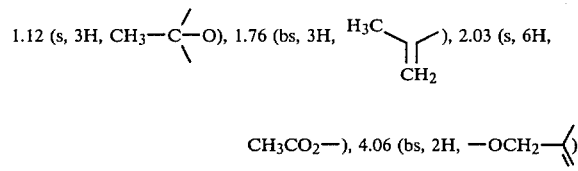), 2.03 (s, 6H,

CH₃CO₂—), 4.06 (bs, 2H, —OCH₂—).

EXAMPLE 15

2S*, 3R*-3-Acetoxy-6E-(2-acetoxyethylidene)-2-methyl-2-(4,8-dimethyl-5-oxo-7-nonenyl)-oxepane A mixture of 2S*, 3R*-acetoxy-6E-(2-acetoxyethylidene)-2-methyl-2-(4,8-dimethyl-5-oxo-8-nonenyl)-oxepane (11 mg), rhodium (III) 2,4-pentandionate (1.2 mg) and tetrahydrofuran (2 ml) is heated under nitrogen at 70° C. for 30 min. The mixture is cooled, treated with ether (20 ml) and washed with 5% sodium bicarbonate solution (2×10 ml). The organic phase is dried (Na₂SO₄), evaporated and the residue is purified by column chromatography on silica gel (5 g, 30% ether in petroleum ether) to give 2S*, 3R*-3-acetoxy-6E-(2-acetoxyethylidene)-2-methyl-2-(4,8-dimethyl-5-oxo-7-nonenyl)-oxepane as a colorless oil (8 mg).

ir (neat), 1739, 1715 cm⁻¹; nmr (CDCl₃)δ: 1.06 (d, J=7 Hz, 3H,

—CH—CH₃); 1.14 (s, 3H, —O—C—CH₃); 1.60 and 1.70 [each s, 3H, HC=C—(CH₃)₂]; 2.03 (s, 6H, —OCO—CH₃); 3.11 (d, J=8 Hz, 2H, —CH₂—C);
                                              ‖
                                              O 4.08 (s, 2H, —CH₂—O—C—), 4.60 (d, J=8 Hz, 2H,

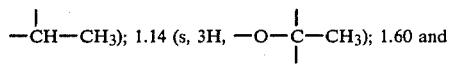C=CH—CH₂—OCOCH₃); 4.80 (m, 1H, 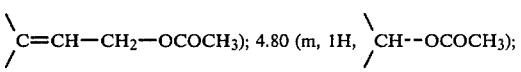CH—OCOCH₃);

5.1–5.5 (m, 2H, (CH₃)₂—C=CH, 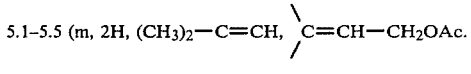C=CH—CH₂OAc.

EXAMPLE 16

2S*, 3R*-3-Acetoxy-6E-(2-acetoxyethylidene)-2-methyl-2-(4-carboxypentyl)-oxepane An excess of Jones reagent is added dropwise to a solution of 2S*, 3R*-3-acetoxy-6E-(2-acetoxyethylidene)-2-methyl-2-(4-methyl-5-oxopentyl)-oxepane (100 mg, 0.28 mmole) in acetone (5 ml) at 0° C. under nitrogen. The mixture is stirred for 1 hr., treated with 2-propanol (2 ml) and allowed to warm to room temperature. The resulting mixture is treated with water (10 ml) and extracted with ethyl acetate (3×20 ml). The combined organic extracts are dried (Na₂SO₄), evaporated and the residue (90 mg) is used directly in the next step without further purification.

ir (neat), 3300—2400 (broad), 1750 (shoulder) 1730 cm⁻¹.

EXAMPLE 17

2S*, 3R*-6E-(2-Hydroxyethylidene)-2-methyl-2-(4,8-dimethyl-5-oxo-7-nonenyl)-oxepan-3-ol An excess of 3-methyl-2-butenyl lithium is added to a mixture of the product obtained in Example 16 (90 mg) and ether (30 ml) at 0° C. under argon. After the addition is complete, the mixture is allowed to warm to room temperature and stirred for 1 hr. The resulting mixture is treated with a saturated ammonium chloride solution (5 ml) and water (20 ml). The organic layer is separated and the aqueous layer is extracted with ethyl acetate (3×20 ml). The combined extract is dried (Na₂SO₄), evaporated, and the residue is purified by column chromatography on silica gel (25 g, ether) to give 2S*, 3R*-6E-(2-hydroxyethylidene)-2-methyl-2-(4,8-dimethyl-5-oxo-7-nonenyl)-oxepan-3-ol as a colorless oil (15 mg, 30%). The ir, nmr spectra, R_f on thin layer and retention time on gas chromatography are identical to the data described for the natural product as reported in U.S. Pat. No. 4,086,358 (as shown in Example 25).

EXAMPLE 18

3-Methyl-4-(tetrahydropyran-2-yloxy)-1-butene (a) To a suspension of magnesium turnings (50.4 g, 2.1 m) in ether (1500 ml) under a nitrogen atmosphere is added a solution of crotyl bromide (135.0 g, 1.0 m) in ether (125 ml), at room temperature over a period of four hours. The reaction mixture is then cooled to 0° C. and formaldehyde [formed by pyrolysis of paraformaldehyde (45.0 g, 0.5 ml)] is bubbled through the mixture. The resulting mixture is allowed to come to room temperature and stirred overnight. The reaction mixture is then decanted into a solution of ammonium chloride (212 g, 4.0 m) in ice water (2 l). The mixture is extracted with ether (2×3000 ml) and the combined ether extracts are dried (Na$_2$SO$_4$) and filtered. The solvent is removed in vacuo to give 57.2 g of 2-methyl-3-buten-1-ol (66%); nmr (CDCl$_3$,δ): 0.99 (d, J=7 Hz, 3H,

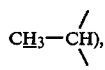

2.10–2.70 (m, 1H,

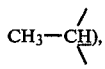

3.30–3.60 (bd, J=6 Hz, 2H,

4.83–6.13 (m, 3H, vinyl protons); ir(neat): 3257, 1640 cm$^{-1}$.

(b) A solution of 2-methyl-3-buten-1-ol (54.16 g, 0.63 m), dihydropyran (52.92 g, 0.63 m), and p-toluenesulfonic acid (0.5 g) in ether (800 ml) is stirred at room temperature under a nitrogen atmosphere overnight. The reaction mixture is then diluted with ether (1 l) and washed with 5% sodium bicarbonate solution (1 l). The ether extract is dried (Na$_2$SO$_4$), filtered and solvent removed in vacuo to give 95.8 g of crude product. The crude product is purified by column chromatography on silica gel (500 g, hexane) to give (75%) 3-methyl-4-(tetrahydropyran-2-yloxy)-1-butene (80.62 g).

nmr: (CDCl$_3$,δ): 1.05 (d, J=6 Hz, 3H, C$\underline{H}_3$CH), 1.33–2.00 (m,

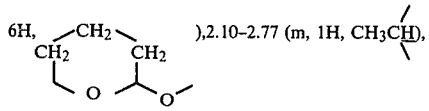

),2.10–2.77 (m, 1H, CH$_3$C$\underline{H}$),

-continued 3.03–4.10 (m, 4H, —C$\underline{H}_2$OC$_5$H$_9$O, 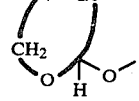 ), 4.57 (bs, 1H, —OCHO—), 4.77–6.13 (m, 3H, vinyl protons);

ir (neat): 1643 (cm$^{-1}$).

EXAMPLE 19

1-Bromo-3-methyl-4-(tetrahydropyran-2-yloxy)-butane

Diborane in tetrahydrofuran (125 ml, 0.150 m) at 0° C. under nitrogen is added to a mixture of 3-methyl-4-(tetrahydropyran-2-yloxy)-1-butene (72 g, 0.423 m) and tetrahydrofuran (150 ml). After the addition is complete, the mixture is allowed to warm to room temperature and then stirred for 1 hour. The reaction mixture is cooled to 0° and bromine (24 ml, 0.43 mmole) and sodium methoxide (0.565 m) in methanol (300 ml) are added slowly simultaneously. After the addition is complete, the mixture is allowed to warm to room temperature and stirred for 30 minutes. The mixture is then treated with water (100 ml) and extracted with petroleum ether (2×200 ml). The organic layer is washed with 5% sodium bicarbonate (100 ml), water (2×100 ml) and dried (Na$_2$SO$_4$). The solvent is removed in vacuo to give a colorless liquid. This crude product is purified by column chromatography in silica gel (500 g, 1% ether in petroleum ether) to give 1-bromo-3-methyl-4-(tetrahydropyran-2-yloxy)-butane (71 g, 65%) as a colorless liquid.

nmr (CDCl$_3$)δ: 1.0 (d, J=6 Hz, 3H,

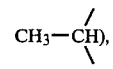

4.59 (br, 1H,

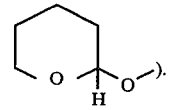

EXAMPLE 20

1-Acetoxy-3-acetoxymethyl-7,11-dimethyl-6,7-oxido-12-(tetrahydropyran-2-yloxy)-2-(E)-dodecene 1-Bromo-3-methyl-4-(tetrahydropyran-2-yloxy)-butane (20 g, 80 mmole) is added to a suspension of magnesium turnings (2.4 g, 100 mmole) in tetrahydrofuran (100 ml) at room temperature under nitrogen over a period of four hours.

An excess of the Grignard reagent prepared above is added to a solution of 7-methyl-3-hydroxymethyl-6,7-oxido-8-tosyloxy-(E)-2-octen-1-yl (950 mg, 2.67 mmole) in tetrahydrofuran (5 ml) followed by Li$_2$CuCl$_4$ (0.1 mmole) at 0° and the resulting mixture is stirred for 4 hrs. The mixture is allowed to warm to room temperature treated with acetic anhydride (2 ml) and stirred overnight. The solvent is removed in vacuo and the residue is purified by column chromatography on silica gel (30 g, 40% ether in petroleum ether) to give 1-acetoxy-3-acetoxymethyl-7,11-dimethyl-6,7-oxido-12-(tetrahydropyran-2-yloxy)-2-(E)-dodecene (301 mg, 25%) as a colorless oil.

ir (neat): 1735 cm$^{-1}$; nmr (CDCl$_3$)δ: 0.95 (d, J=6 Hz, 3H,

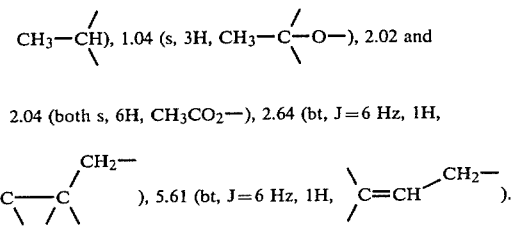

2.04 (both s, 6H, CH$_3$CO$_2$—), 2.64 (bt, J=6 Hz, 1H,

EXAMPLE 21

2S*, 3R*-3-Acetoxy-6E-(2-acetoxyethylidene)-2-methyl-2-[4-methyl-5-(tetrahydropyran-2-yloxy)pentyl]oxepane A mixture of 1-acetoxy-3-acetoxymethyl-7,11-dimethyl-6,7-oxido-12-(tetrahydropyran-2-yloxy)-2(E)-dodecene (512 mg, 1.16 mmole), methanol (20 ml) and saturated potassium carbonate (1 ml) is stirred at room temperature for 4 hours under nitrogen. Most of the solvent is removed in vacuo and the residue is filtered through a silica gel column (10 g) and washed with ether (100 ml). The solvent is removed in vacuo to give the compound 3-hydroxymethyl-7,11-dimethyl-6,7-oxido-12-(tetrahydropyran-2-yloxy)-2(E)-dodecen-1-ol (410 mg) as a colorless oil. The oil is redissolved in methylene chloride (20 ml) and treated with trifluoroacetic acid (2 drops). The resulting mixture is stirred for 30 minutes, treated with pyridine (2 ml) and acetic anhydride (1.5 ml) and allowed to stir overnight. The solvent is removed in vacuo and the residue is purified by column chromatography on silica gel (10 g, 25% ether in petroleum ether) to give 2S*, 3R*-3-acetoxy-6E-(2-acetoxyethylidene)-2-methyl-2-[4-methyl-5-(tetrahydropyran-2-yloxy)pentyl]oxepane (130 mg, 25%) as a colorless oil.

ir (neat): 1735 cm$^{-1}$; nmr (CDCl$_3$)δ: 0.95 (d, J=6 Hz,

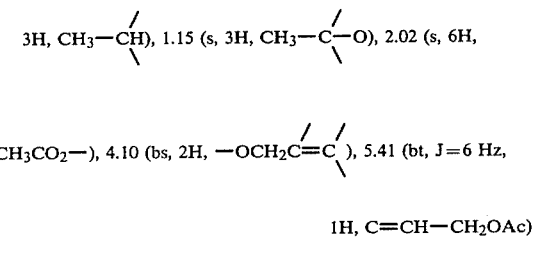

1H, C=CH—CH$_2$OAc).

EXAMPLE 22

2S*, 3R*-3-Acetoxy-6E-(2-acetoxyethylidene)-2-methyl-2-(4-methyl-5-hydroxypentyl)-oxepane A mixture of 2S*,3R*-3-acetoxy-6E-(2-acetoxyethylidene)-2-methyl-2-[4-methyl-5-(tetrahydropyran-2-yloxy)pentyl]-oxepane (70 mg, 0.16 mmole), water (0.5 ml), tetrahydrofuran and acetic acid (5 ml) is heated at 50° C. under nitrogen. Most of the solvent is removed in vacuo and the residue is filtered through a silica gel column and washed with ether (200 ml). The solvent is removed in vacuo to give 2S*,3R*-3-acetoxy-6E-(2-acetoxyethylidene)-2-methyl-2-(4-methyl-5-hydroxypentyl)-oxepane (55 mg, 92%) as a colorless oil.

ir (neat) 3350, 1730 cm$^{-1}$; nmr (CDCl$_3$)δ: 0.93 (d,

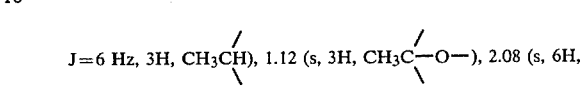

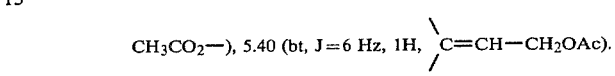

EXAMPLE 23

2S*,3R*-3-acetoxy-6E-(2-acetoxyethylidene)-2-methyl-2-(4-carboxypentyl)-oxepane

An excess of Jones reagent (10 mmole) is added slowly to a mixture of 2S*,3R*-3-acetoxy-6E-(2-acetoxyethylidene)-2-methyl-2-[4-methyl-5-(tetrahydropyran-2-yloxy)pentyl]oxepane (130 mg, 0.29 mmole) and acetone (3 ml) at 0° C. under nitrogen. After the addition is complete the mixture is warmed to room temperature and stirred for 3 hours. The mixture is then treated with ethyl acetate (50 ml) and the organic phase is washed with water (3×10 ml) and then dried (Na$_2$SO$_4$). The solvent is removed in vacuo to give 2S*,3R*-3-acetoxy-6E-(2-acetoxyethylidene)-2-methyl-2-(4-carboxypentyl)-oxepane (130 mg) as a pale yellow oil.

EXAMPLE 24

2S*,3R*-3-acetoxy-6E-(2-acetoxyethylidene)-2-methyl-2-(4-methyl-5-oxo-pentyl)-oxepane A mixture of 2S*,3R*-3-acetoxy-6E-(2-acetoxyethylidene)-2-methyl-2-(4-methyl-5-hydroxypentyl)oxepane (47 mg, 0.136 mmole) and methylene chloride (5 ml) is added to an excess of chromium trioxide-pyridine complex in methylene chloride (10 ml) at 0° C. under nitrogen. The resulting mixture is stirred for 90 minutes and filtered. The filtrate is washed with saturated sodium bicarbonate solution (20 ml)) and dried (Na$_2$SO$_4$). The solvent is removed in vacuo to give a pale yellow oil. This material is purified by column chromatography on silica gel (5 g, 30% ether in petroleum ether) to give 2S*,3R*-3-acetoxy-6E(2-acetoxyethylidene)-2-methyl-2-(4-methyl-5-oxopentyl)-oxepane (41 mg, 90%) as a colorless oil.

ir (neat): 2660, 1740 (shoulder), 1735 cm$^{-1}$.

EXAMPLE 25

2S*,3R*-6E-(2-Hydroxyethylidene)-2-methyl-2-(4,8-dimethyl-5-oxo-7-nonenyl)-oxepane-3-ol The 2S*, 3R*-3-acetoxy-6E-(2-acetoxyethylidene)-2-methyl-2-(4,8-dimethyl-5-oxo-7-nonenyl)-oxepane (161 mg) obtained above (Example 15) is dissolved in tetrahydrofuran (5 ml) and water (5 ml). To this mixture, tetra n-butyl ammonium hydroxide (20% solution in methanol, 1 ml) is added under nitrogen at room temperature and the resulting mixture is stirred for 40 hours. The mixture is treated with ether (50 ml) and the organic layer is washed with 10% hydrochloric acid (2×15 ml), dried (MgSO₄) and evaporated in vacuo to give an oil. This crude product is purified by chromatography on a SilicAR column (5 g). The product 2S*, 3R*-6E-(2-hydroxyethylidene)-2-methyl-2-(4,8-dimethyl-5-oxo-7-nonenyl)-oxepane-3-ol (81.8 mg), is eluted with ether. Its ir, nmr spectra, $R_f$ on thin layer and retention time on gas chromatography are identical to those of the natural product reported in U.S. Pat. No. 4,086,358. The compound has the following physical analysis:

ir (neat) μ: 2.91 and 5.88; nmr $\frac{CDCl_3\delta:}{TMS}$ 5.41 (m, 2H,

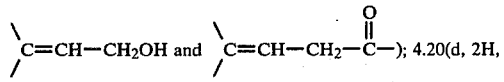); 4.20(d, 2H,

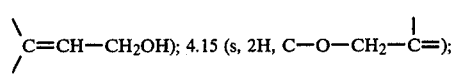); 4.15 (s, 2H, C—O—CH₂—C=);

3.58 [broad t, 1H, CH OH]; 3.18 (d, 2H, 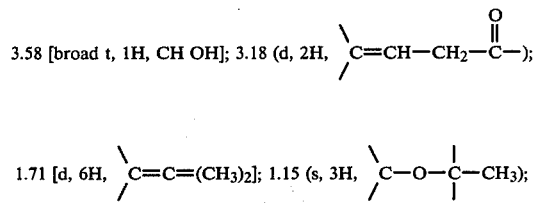

1.71 [d, 6H, \C=C=(CH₃)₂]; 1.15 (s, 3H, \C—O—C—CH₃);

Mass spec [m/e]: 320 [M-18], 251, 233, 221, 171, 143, 141, 137, 125, 113, 97, 95, 81, 69; Chemical ionization:

M⁺ + H = 339: M.W. = 338.

What is claimed is:
1. The process for the preparation of a compound of the formula

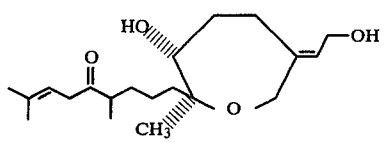

which comprises reacting a compound of the formula

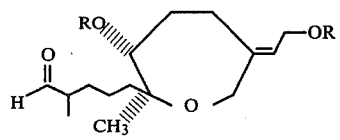

with a compound of the formula

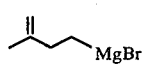

to form a compound of the formula

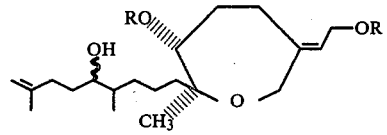

reacting the product formed with an oxidizing agent selected from chromium trioxide-sulfuric acid and chromium trioxidepyridine to form a ketone of the formula

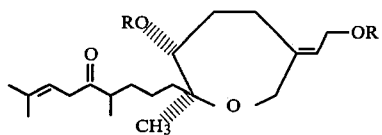

isomerizing the product with rhodium (III) 2,4-pentadionate to form a compound of the formula

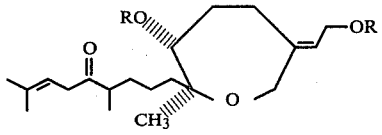

and hydrolyzing the ester with a base, wherein R is an acyl group having 2–5 carbon atoms.

2. The process of claim 1 wherein the oxidizing agent is chromium trioxide—sulfuric acid.

3. The process of claim 1 wherein R is acetyl.

4. The process for the preparation of a compound of the formula

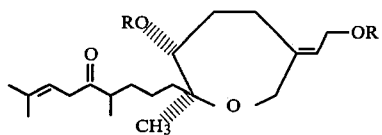

which comprises reacting a compound of the formula

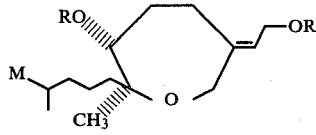

with a protic acid to form a compound of the formula

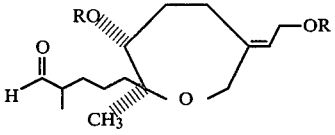

reacting the product formed with a compound of the

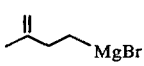

to form a compound of the formula

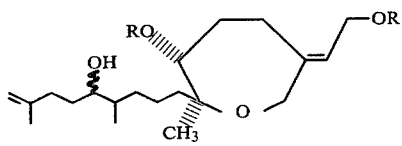

reacting the product formed with an oxidizing agent selected from chromium trioxide-sulfuric acid and chromium trioxidepyridine to form a ketone of the formula

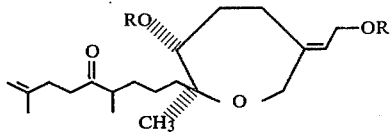

isomerizing the ketone with rhodium (III) 2,4-pentadionate to form a compound of the formula

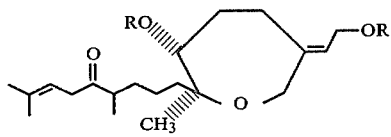

and hydrolyzing the ester with a base, wherein R is an acyl group having 2-5 carbon atoms and M is selected from the group consisting of ethylenedioxymethyl, 4-methyl-1,3-ethylenedioxymethyl, 1,3-propylenedioxymethyl.

5. The process of claim 4 wherein the oxidizing agent is chromium trioxide-sulfuric acid.

6. The process of claim 4 wherein R is acetyl and M is ethylenedioxymethyl.

* * * * *